(12) United States Patent
Crich et al.

(10) Patent No.: US 6,960,654 B2
(45) Date of Patent: Nov. 1, 2005

(54) METHOD OF FORMING GLYCOSIDIC BONDS FROM THIOGLYCOSIDES USING AN N,N-DIALKYLSULFINAMIDE

(75) Inventors: David C. Crich, Chicago, IL (US); Mark Smith, Chicago, IL (US)

(73) Assignee: The Board of Trustees of the University of Illinois, Urbana, IL (US)

(*) Notice: Subject to any disclaimer, the term of this patent is extended or adjusted under 35 U.S.C. 154(b) by 131 days.

(21) Appl. No.: 10/452,734

(22) Filed: Jun. 2, 2003

(65) Prior Publication Data

US 2004/0019198 A1 Jan. 29, 2004

Related U.S. Application Data

(60) Provisional application No. 60/387,806, filed on Jun. 11, 2002.

(51) Int. Cl.[7] .......................... C07G 3/00; C07H 15/00; C07H 17/00
(52) U.S. Cl. ...................... 536/18.5; 536/4.1; 536/17.2; 536/17.5; 536/124; 536/1.11
(58) Field of Search ................................ 536/4.1, 17.2, 536/17.5, 18.5, 124, 1.11

(56) References Cited

FOREIGN PATENT DOCUMENTS

JP          07252289 A    *  10/1995

OTHER PUBLICATIONS

D. Crich et al., *J. Org. Chem.*, published on Web, six pages. (2001).
D. Crich et al., *Tetrahedron*, 58, pp. 35–44 (2002).
D. Crich et al., *J. Am Chem. Soc.*, vol. 123, No. 37, pp. 9015–9020 (2001).
J.D.C. Codee et al., *Organic Letters*, vol. 5, No. 9, pp. 1519–1522 (2003).

* cited by examiner

*Primary Examiner*—James O. Wilson
*Assistant Examiner*—Everett White
(74) *Attorney, Agent, or Firm*—Marshall, Gerstein & Borun LLP

(57) ABSTRACT

A method of forming a glycosidic bond utilizing an activated thioglycoside is disclosed. The thioglycoside is activated by an N,N-dialkylsulfinamide and trifluoromethanesulfonic anhydride. The method allows the facile synthesis of disaccharides, oligosacchraides, and polysaccharides in solution or on a polymer support.

19 Claims, No Drawings

METHOD OF FORMING GLYCOSIDIC BONDS FROM THIOGLYCOSIDES USING AN N,N-DIALKYLSULFINAMIDE

CROSS-REFERENCE TO RELATED APPLICATIONS

This application claims the benefit of U.S. provisional patent application Ser. No. 60/387,806, filed Jun. 11, 2002.

STATEMENT OF GOVERNMENTAL INTEREST

This research was supported by Grant No. 1R01 GM57335 from the National Institutes of Health, Bethesda, Md. The government has certain rights to this invention.

FIELD OF THE INVENTION

The present invention relates to a method of forming glycosidic bonds. More particularly, the present invention relates to methods of forming glycosidic bonds, either in solution or on a polymer support, from a thioglycoside utilizing an N,N-dialkylsulfinamide and trifluoromethanesulfonic anhydride ($Tf_2O$). The present method permits the facile formation of several different types of glycosidic bonds, and can be utilized in an automated syntheses of oligosaccharides and polysaccharides.

BACKGROUND OF THE INVENTION

Carbohydrates play a central role in a wide variety of normal and abnormal biological recognition processes. For example, oligosaccharides and polysaccharides, as components of glycoproteins and glycolipids, are ubiquitous on cell surfaces and function as cell-surface markers for recognition by protein receptors. Although such carbohydrate-mediated interactions are important in biological events, an understanding of the structure-activity relationships (SAR) of carbohydrates has developed very slowly because of the difficulty of synthesizing well-defined oligosaccharides and polysaccharides for study.

For example, carbohydrates on cell surfaces have been implicated in chronic inflammation, in viral and bacterial infection, and in tumorigenesis and metastasis. Inhibiting interactions between cell surface carbohydrates and their protein receptors could provide an effective means of preventing or treating various diseases. Consequently, a great potential exists for, and a great amount of research is directed to, the use of synthetic oligosaccharides and polysaccharides as therapeutic agents.

One application of synthetic oligosaccharides is inhibition of cell adhesion. Thus, there is interest in synthetic carbohydrates that interfere with selectin and/or integrin binding, and, therefore, of use in the treatment of asthma, ARDS, reperfusion injury, multiple sclerosis, and various other chronic inflammatory diseases.

Synthetic carbohydrates also can be useful to inhibit bacterial adhesion to human tissue. Certain oligosaccharides and polysaccharides also can be useful to induce immune responses, for antibody production, e.g., as vaccines, or to induce disease states in research animals.

Despite such uses of synthetic oligosaccharides and polysaccharides in research and therapeutic applications, no universally applicable method exists for the synthesis of these complex molecules presently. Enzymatic methods have been developed that are effective in the regiospecific and stereospecific formation of glycosidic linkages, but the enzymes are relatively specific for particular substrates, and are not widely applicable to the variety of oligosaccharides and polysaccharides that must be synthesized. See, O. Karthaus et al. *J. Chem. Soc. Perkin Trans.*, 1, 1851–1857 (1994), and M. Schuster et al., *J. Amer. Chem. Soc.*, 116, 1135 (1994).

Oligosaccharide synthesis is not limited to an enzymatic method, and, therefore, carbohydrate synthesis has become a very active field of research. Other glycosylation reactions and strategies for carbohydrate synthesis have been developed. As a result, some relatively complex oligosaccharides have been synthesized, but to date no generally applicable "universal" synthetic method that can reliably generate glycosidic linkages with control of regiochemistry and stereochemistry exists.

Persons skilled in the art are aware that subtle changes in the structures of glycosyl donors and acceptors change the regiochemical and stereochemical outcomes, and the yields, of existing glycosylation reactions. Consequently, every oligosaccharide synthesis is a unique undertaking. The state of the art, therefore, does not permit the synthesis of large libraries of oligosaccharides for screening purposes Combinatorial synthesis has been used to identify drug leads and elucidate structure-activity relationships in specific areas of drug discovery. Combinatorial methods of synthesizing peptides and nucleic acids on solid supports to provide combinatorial libraries of peptides and nucleic acids have been available for many years. But, combinatorial methods to synthesize carbohydrates on the solid phase only now are being developed. See Liang et al., *Science*, 274, pp. 1520–1522 (1996). The reliable preparation of a combinatorial oligosaccharide library requires reliable and consistently If high-yielding reactions, which give well-defined products from a variety of substrates under standardized reaction conditions.

Carbohydrates are notoriously difficult to synthesize, but research groups have made advances in simplifying and accelerating the synthetic process. For example, an automated solid-phase oligosaccharide synthesizer that facilitates preparation of carbohydrates has been developed (*Science*, 291, 1523 (2001)). The automated oligosaccharide synthesis allows production of oligosaccharides in about 1% of the time required using previous methods.

A comprehensive carbohydrate-based combinatorial capability requires an ability to link, attach, and modify sugars. However, the execution of such a comprehensive strategy is difficult because of the complexity of carbohydrate-based systems and the synthetic difficulties related to their construction and modification.

In addition, a simple monosaccharide contains multiple reactive sites and an anomeric center with difficult-to-control stereochemistry. Traditionally, a site selective reaction is controlled by complicated protecting group schemes. Further, the construction of multiple consecutive glycosidic linkages or glycosidic linkages to differing substrates typically relied upon different glycosylating reagents because of the lack of a single general glycosidic bond-forming reaction reliably applicable to a wide variety of substrates. Therefore, the success of a carbohydrate-based combinatorial program depends on effectively solving the unique chemical problems posed by carbohydrates.

The linking of monosaccharide units through a glycosidic bond is fundamental to the synthesis of oligosaccharides and various glycoconjugates. Therefore, the development of carbohydrate-based technology requires the construction of glycosidic bonds in the solid or liquid phase. The formation of glycosidic bonds is central to the field of glycobiology and to the preparation of a carbohydrate-based therapeutic or diagnostic agent.

Thioglycosides are among the most widely used glycosyl donors because of their ease of preparation and shelf stability. Thioglycosides also are compatible with numerous protection and deprotection synthetic steps, as well as being orthogonal to several other glycosidic bond-forming reactions, such as the trichloroacetimidate and glycosyl fluoride methods. See, P. J. Garegg, *Carbohydr. Chem. Biochem.*, 52, pp. 179–266 (1997).

A thioglycoside requires activation to form a glycosidic bond. However, the stability that renders thioglycosides attractive as a donor, sufficiently reduces their reactivity in coupling reactions such that reaction times often are very long (e.g., up to ten days). Current methods of activating thioglycosides also suffer from one or more other disadvantages, such as unstable or unavailable activating agents, the need to oxidize the thioglycoside to the sulfoxide, poor stereoselectivity, and lack of generality. In addition, expensive reagents, which typically suffer from stability problems, are required for activation. Frequently, reagents used to activate thioglycosides are based on heavy (e.g., mercury) or precious (e.g., silver) metals, and pose problems of expense, environmental and toxicological concerns, and/or disposal.

Nonmetallic thiophiles of varying stability and activity currently in common use include dimethyl(methylthio)sulfonium triflate (DMTST), methylsulfenyl triflate (MeSOTf), benzeneselenyl triflate (PhSeOTf), iodonium dicollidine perchlorate (IDCP), and N-iodosuccinimide-trifluoromethane sulfonic acid (NIS/TfOH). Kahne's sulfoxide glycosylation method (D. Kahne et al., *J. Am. Chem. Soc.*, 111, 6881–6882 (1989)) and related methods using glycosyl sulfimides (S. Cassel et al., *Tetrahedron Letters*, 39, 5175–5178 (1998)) are distinct from the mainstream methods because these methods require prior oxidation of the thioglycoside but, in doing so, permit the formation of highly reactive glycosylating species at low temperature.

Investigators, therefore, are searching for improved methods of activating thioglycosides, and forming of glycosidic bonds in general. One research group has developed a polymer-supported synthesis of oligosaccharides (O. J. Plante et al., *Science*, 291. pp. 1523–1527 (2001)). However, this technology does not permit the preparation of β-mannosides, and also utilizes a very unstable glycosyl phosphate and/or trichloroacetimidate.

The present invention provides a method of forming glycosidic bonds utilizing thioglycosides and an activating system that overcomes problems associated with prior methods of forming glycosidic bonds, and permits the automated synthesis of oligosaccharides and polysaccharides.

SUMMARY OF THE INVENTION

The present invention is directed to an improved method of forming glycosidic bonds, which in turn facilitates the synthesis, including the automated synthesis, of oligosaccharides and polysaccharides, in solution and in the solid phase. More particularly, the present invention is directed to utilizing a thioglycoside to form a glycosidic bond, wherein the thioglycoside is activated using an N,N-dialkylsulfinamide and trifluoromethanesulfonic anhydride ($Tf_2O$).

Therefore, one aspect of the present invention is to provide an activating system for thioglycosides that can be used in the formation of glycosidic bonds and in the synthesis of oligosaccharides and polysaccharides. The thioglycoside-activating system of the present invention:

(i) is useful in the formation of a very wide range of glycosidic bonds, including, but not limited to, β-mannosides, 2-deoxy-2-aminoglucosides, and galactosides;

(ii) is compatible with both armed (ether protected) and disarmed (ester protected) thioglycosides;

(iii) enables coupling to primary, secondary, and tertiary alcohols, and primary and secondary amines, as glycosyl acceptors;

(iv) functions in minutes, e.g., about 2 to about 10 minutes, at low temperatures, e.g., about −50° C. to about −78° C.;

(v) uses a combination of commercially available trifluoromethanesulfonic anhydride and a readily prepared N,N-dialkylsulfinamide as the thioglycoside activating system; and (vi) functions in an extremely efficient manner for the low temperature activation of insoluble polymer supported thioglycosides.

Another aspect of the present invention is to provide a method of synthesizing β-mannosides on a polymer support.

Still another aspect of the present invention is to provide a method of activating a thioglycoside comprising adding $Tf_2O$ and an N,N-dialkylsulfinamide having a general structural formula (I):

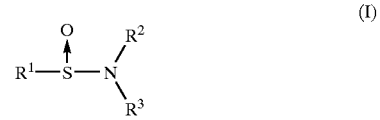

(I)

wherein $R^1$ is selected from the group consisting of aryl, heteroaryl, and $C_{1-6}$alkyl; and $R^2$ and $R^3$, independently, are $C_{1-6}$alkyl, or $R^2$ and $R^3$ are taken together with the nitrogen atom to which they are attached to form a 4- to 8-membered aliphatic ring, optionally containing an additional nitrogen, oxygen, or sulfur atom, to the thioglycoside.

Another aspect of the present invention is to provide an activating system for a selenoglycoside comprising $Tf_2O$ and an N,N-dialkylsulfinamide.

Another aspect of the present invention is to provide an activating system for a thioglycoside comprising $Tf_2O$ and either a solid N,N-dialkylsulfinamide having a structure

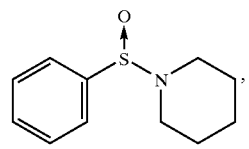

or a liquid N,N-dialkylsulfinamide having a structure

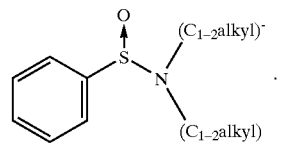

Yet another aspect of the present invention is to provide a method of converting an —SR moiety (wherein R is alkyl or aryl) of a thioglycoside to an —OR''', —NH(R'''), or —N(R''')$_2$ moiety, wherein R''', independently, is a moiety of a simple or complex alcohol or amine of structure R'''OH, $NH_2$ (R'''), or NH(R''')$_2$, respectively.

Still another aspect of the present invention is to provide a combination of 1-benzenesulfinyl piperidine (BSP) and trifluoromethanesulfonic anhydride (Tf$_2$O) as a powerful, metal-free thiophile that can readily activate both armed and disarmed thioglycosides, via glycosyl triflates in about 2 to about 10 minutes at about −50° C. to about −78° C., e.g., at −60° C., in a suitable solvent, e.g., dichloromethane, and, optionally, in the presence of a suitable base, e.g., 2,4,6-tri-tert-butylpyrimidine (TTBP). The glycosyl triflates are rapidly and efficiently converted to glycosides, upon treatment with acceptor alcohols and amines, in good yield and stereochemical selectivity.

These and other novel aspects and advantages of the present invention will become apparent from following detailed description of the preferred embodiments.

DETAILED DESCRIPTION OF THE PREFERRED EMBODIMENTS

A primary goal of research in the carbohydrate area has been the development of more practical activators capable of converting thioglycosides to glycosyl triflates at low temperature. The present invention is directed to the use of an activating system comprising an N,N-dialkylsulfinamide and Tf$_2$O, which activates thioglycosides (or selenoglycosides) in about 2 to about 10 minutes at about −50° C. to about −78° C., and thereby facilitates the formation of glycosidic linkages.

The use of S-aryl arylthiosulfinates, in conjunction with Tf$_2$O, as activating agents for armed thioglycosides has been disclosed in D. Crich et al., *Org. Lett.*, pp. 4067–4069 (2000). However, the disclosed activating system did not permit activation of disarmed thioglycosides. (i.e., thioglycosides protected with ester groups), and required several equivalents of reagents for complete activation of armed thioglycosides (i.e., thioglycosides protected with ether groups).

The present thioglycoside activating system comprises an N,N-dialkylsulfinamide as a shelf-stable reagent that is substantially more powerful than the previously described activating systems, requires only a minimal excess, if any, of Tf$_2$O over a stoichiometric amount, and activates both armed and disarmed thioglycosides. The present activating system converts thioglycosides to glycosyl triflates, and eventually to glycosidic bonds, cleanly and in high yield.

It should be understood that a present activating system also activates selenoglycosides. Accordingly, the term "thioglycoside" as used herein refers collectively to thioglycosides and selenoglycosides.

The N,N-dialkylsulfinamides used in the present activating system are known compounds. See, T. J. Maricich et al., *J. Org. Chem.*, 49, pp. 1931–1934 (1985), and K. K. Andersen, *Comprehensive Organic Chemistry*, D. H. R. Barton and W. D. Ollis, eds., Pergamon, Oxford, Vol. 3, pp. 317–329 (1979). However, N,N-alkylsulfinamides have not been utilized as an activator component for thioglycosides, or in the reactions disclosed herein. Also, the reaction between N,N-dialkylsulfinamides and Tf$_2$O has not been reported previously. Boronic acid functionalized polymers for use in solid phase oligosaccharide synthesis has been disclosed, but not employed previously in the synthesis of β-mannosides. See, G. Belogi et al., *Tetrahedron Lett.*, 41, pp. 6965–6968 (2000).

The present invention utilizes a thioglycoside as the donor, and overcomes the disadvantages associated with other glycosylation methods using a thioglycoside or other donor. The present invention allows activation of thioglycosides within minutes at about −50° C. to about −78° C., and typically at about −60° C. to about −78° C., using a combination of two, metal-free, shelf-stable reagents, one of which (Tf$_2$O) is commercially available and the other (an N,N-dialkylsulfinamide) is easily prepared synthetically on a large scale. Moreover, all types of thioglycosides, i.e., armed and disarmed, are activated in accordance with the present invention under a standard set of conditions, and a wide range of different glycosidic bonds can be formed.

The present method can be used to activate polymer-supported or solubilized thioglycosides with several advantages, including ease of operation, purification, and automation. The present method also can be used to form the widest possible range of glycosidic bonds in a highly efficient manner. It is envisioned that the method can be extended to encompass the formation of other types of glycosidic bonds, such as more elaborate thioglycosides, N-glycosides (nucleosides), and C-glycosides.

L. Yan et al., *J. Am. Chem. Soc.*, 118, pp. 9239–9248 and U.S. Pat. No. 6,040,433 disclose a method that requires prior oxidation of a thioglycoside to the sulfoxide, but has not been widely applied. The most widely applied glycosylation method, i.e., the trichloroacetimidate method disclosed in R. R. Schmidt et al., *Adv. Carbohydr. Chem. Biochem.*, 50, pp. 21–123 (1994), requires the preparation and use of unstable glycosyl trichloroacetimidates, and, therefore, is significantly less convenient than a method based on the use of thioglycosides.

The glycosyl fluoride method can be compared to the present thioglycoside method because glycosyl fluorides are readily prepared and shelf stable, but this method is of no economic interest because the activating elements are metal based, typically using hafnium, which severely limits commercial application. See, K. C. Nicolaou et al., "Oligosaccharide Synthesis from Glycosyl Fluorides and Sulfides," in *Preparative Carbohydrate Chemistry*, S. Hanessian, ed., Dekker, N.Y., pp. 313–338 (1997).

For the purposes of this disclosure, the following terms are defined as follows.

The term "monosaccharide" refers to a pentose, hexose, heptose, or octose sugar, analog, or derivative thereof, including, but not limited to, deoxy sugars, dideoxy sugars, amino sugars, and sugar acids. The term includes protected and unprotected forms of monosaccharides, i.e., wherein selected reactive groups, typically oxygen- or nitrogen-bearing groups, of the monosaccharide have been either temporarily blocked ("protected") to prevent their undergoing a reaction under the conditions of a specific transformation or left exposed and available for possible participation in a reaction, respectively.

The term "glycoconjugate" refers to any molecule, substance, or substrate, such as a solid, including a monosaccharide, carbohydrate, disaccharide, oligosaccharide, or polysaccharide covalently attached or adhered to a nonsugar chemical, biochemical, biological, or inorganic moiety. Preferred glycoconjugates include, but are not limited to, low molecular weight molecules conjugated to the sugar (e.g., heteropolyaromatic-sugar conjugates, nucleosides, nucleoside analogs, and the like), glycopeptides, glycoproteins, and the like.

The term "protecting group" refers to any chemical moiety that is temporarily attached to a reactive functional group of a given molecule to mask functional group reactivity while chemical reactions are permitted to proceed elsewhere on the molecule. Protecting groups preferred for protecting the reactive functional groups of sugars include, but are not limited to, alkyl, benzyl, acyl (erg., benzoyl), and silyl protecting groups. Many other protecting groups are well known to those of ordinary skill in the art.

The term "glycosyl donor" refers to a sugar with a leaving group (or potential leaving group) on at least one anomeric carbon which, under appropriate conditions, is capable of participating in a glycosylation reaction wherein the anomeric carbon becomes covalently attached to a second moiety, typically a glycosyl acceptor, as defined below, or a nucleophile.

The term "glycosyl acceptor" refers to any moiety, including a sugar, having the capacity to participate as the second moiety in the glycosylation reaction by virtue of a nucleophilic (or potentially nucleophilic) group present among the groups or substituents of such moiety, such that a covalent bond is formed between an anomeric carbon of a glycosyl donor and the nucleophilic (or potentially nucleophilic) group.

The terms "carbohydrate, disaccharide, oligosaccharide, or polysaccharide" all refer to a molecule or a portion thereof, which is comprised of two or more monosaccharides that are joined by a glycosidic linkage. A "sugar" is any carbohydrate, disaccharide, oligosaccharide, polysaccharide, or monosaccharide.

The terms "$C_{1-6}$alkyl," and "$C_{1-2}$alkyl" are defined as an alkyl group, straight chain, branched, or bicyclic, containing one to six or one to two, carbon atoms, respectively. The alkyl group optionally can be substituted with one or more, and typically one to three, nonreactive substituents, such as, for example, halo (i.e., Cl, Br, F, I), alkoxy (e.g., $OCH_3$, $OC_2H_5$), $OCF_3$, $CF_3$, aryloxy (e.g., $OC_6H_5$), or aryl (e.g., $C_6H_5$). The term "$C_{2-6}$alkenyl" is defined similarly, except the carbon chain contains a carbon-carbon double bond.

The term "acyl" is defined as RC(=O)—, wherein R is $C_{1-6}$alkyl or aryl.

The term "aryl," alone or in combination, is defined as a monocyclic or polycyclic aromatic group, preferably a monocyclic or bicyclic aromatic group, e.g., phenyl or naphthyl. Unless otherwise indicated, an "aryl" group can be unsubstituted or substituted, for example, with one or more, and in particular, one to four, halo, $C_{1-6}$alkyl, $C_{2-6}$alkenyl, $OCF_3$, $NO_2$, CN, $CF_3$, alkoxy, and aryloxy. Exemplary aryl groups include phenyl, naphthyl, tetrahydronaphthyl, chlorophenyl, methylphenyl, methoxyphenyl, trifluoromethylphenyl, nitrophenyl, 2,4-methoxychlorophenyl, and the like.

The term "heteroaryl" is defined herein as a monocyclic or bicyclic ring system containing one or two aromatic rings and containing at least one nitrogen, oxygen, or sulfur atom in an aromatic ring, and that can be unsubstituted or substituted, for example, with one or more, and in particular one to four, substituents, for example, $C_{1-6}$alkyl, $C_{2-6}$alkenyl, alkoxy, aryl, aryloxy, $OCF_3$, $CF_3$, and halo. Examples of heteroaryl groups include, but are not limited to, thienyl, furyl, pyridyl, oxazolyl, quinolyl, isoquinolyl, indolyl, triazolyl, isothiazolyl, isoxazolyl, imidazolyl, benzbthiazolyl, pyrazinyl, pyrimidinyl, thiazolyl, and thiadiazolyl.

The following abbreviations are used herein: Bn is benzyl, Bz is benzoyl, Ac is acetyl, Ph is phenyl, Me is methyl, and Phth is phthalimide.

A thioglycoside is activated using an N,N-dialkylsulfinamide and $Tf_2O$. The N,N-dialkylsulfinamide has a general structural formula (I):

wherein $R^1$ is selected from the group consisting of aryl, heteroaryl, and $C_{1-6}$alkyl; and $R^2$ and $R^3$, independently, are $C_{1-6}$alkyl, or $R^2$ and $R^3$ are taken together with the nitrogen atom to which they are attached to form a 4- to 8-membered aliphatic ring, optionally containing an additional nitrogen, oxygen, or sulfur atom.

In preferred embodiments, $R^1$ is aryl, and $R^2$ and $R^3$, independently, are $C_{1-2}$alkyl, or $R^2$ and $R^3$ are taken together with the nitrogen to which they are attached to form a 5- or 6-membered aliphatic ring.

In most preferred embodiments, $R^1$ is aryl, preferably phenyl, $R^2$ and $R^3$ both are methyl or both are ethyl, or $R^2$ and $R^3$ are taken together with the nitrogen to which they are attached to form a pyrrolidinyl or, preferably, a piperidinyl moiety.

A preferred N,N-dialkylsulfinamide used in the present invention is 1-benzenesulfinyl piperidine, termed BSP, and having a structural formula

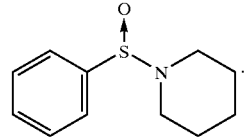

Another preferred N,N-dialkylsulfinamide has the structure:

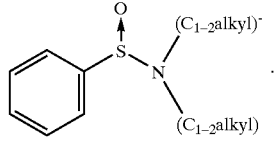

BSP is used in conjunction with $Tf_2O$, and is a potent reagent for the activation of both armed and disarmed thioglycosides. The reaction between BSP and $Tf_2O$ is illustrated below:

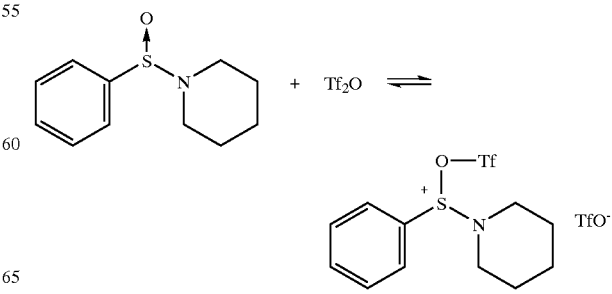

BSP is readily prepared in relatively large scale, is white, crystalline, and readily dried, and is shelf-stable under ambient storage conditions. Moreover, as demonstrated by standard low-temperature NMR experiments, BSP reacts completely with Tf$_2$O and converts a standard thioglycoside (1) to a glycosyl triflate (2) within minutes at −60° C., essentially stoichiometrically.

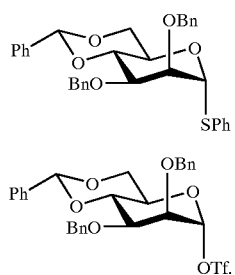

Optimal glycosidic bond formation is achieved simply by cooling a 1:1 mixture of the thioglycoside and an N,N-dialkylsulfinamide of the present invention, e.g., BSP, to −60° C. in dichloromethane (CH$_2$Cl$_2$) in the presence of the hindered base, e.g., 2,4,6-tri-tert-butylpyrimidine (TTBP), treatment with 1.1 equiv. of Tf$_2$O, and, after five minutes, addition of an acceptor alcohol or amine, warming to room temperature, and isolating the product using standard work-up procedures.

The N,N-dialkylsulfinamides are readily prepared in a large scale, for example, by conversion of thiophenol to benzensulfinyl chloride (PhSOCl) using sulfuryl chloride and acetic anhydride, followed by treatment with a desired secondary amine, e.g., piperidine. Many N,N-dialkylsulfinamides are isolated by crystallization to provide a white stable solid. Others are isolated by vacuum distillation to provide clear liquids. The following illustrates the preparation of an N,N-dialkylsulfinamide, specifically BSP.

A solution of PhSOCl (58.9 g, 0.365 mol) in diethyl ether (Et$_2$O) (200 mL) was added slowly to a cooled solution (5° C.) of piperidine (72 mL, 0.73 mol) in Et$_2$O (200 mL). The reaction mixture then was stirred at room temperature for 1 hour, filtered, and concentrated under reduced pressure. The solid residue was triturated with hexanes to yield BSP as a white crystalline solid (53.4 g, 70%): mp 84–85° C. (lit. mp 83–84° C.); $^1$H NMR δ: 1.41–1.53 (6H, m), 2.83–2.87 and 2.89–3.04 (each 2H, m), 7.37–7.42 (3H, m), 7.56–7.59 (2H, m); $^{13}$C NMR δ: 23.8, 26.1, 46.9 126.1, 128.7, 130.6, and 143.3; MS (EI) m/z 210 (MH$^+$).

The trifluoromethanesulfonic anhydride used in the activating system is commercially available, and is used in conjunction with the N,N-dialkylsulfinamide to provide an extremely potent activating system for the formation of glycosidic bonds from thioglycosides.

The N,N-dialkylsulfanilamide is used in an amount of about one mole per one mole of thioglycoside. The Tf$_2$O is used in an amount of about 1 to about 1.2 mole per mole of thioglycoside. The reaction is performed in the presence of an optional base, typically a weak, sterically hindered base, such as 2,6-di-t-butylpyridine, 2,4,6-tri-t-butylpyrimidine, or a similar base known to persons skilled in the art. The reaction also is performed in a solvent, preferably a chlorinated solvent, like dichloromethane, at a temperature of about −50° C. to −78° C., preferably about −55° C. to about −65° C. The identity of the solvent is not limiting, and any solvent that solubilizes the reactants, as desired, and is a liquid at the reaction temperature can be used in the method of the present invention.

The 2,4,6-tri-t-butylpyrimidine (TTBP) is a preferred, sterically hindered, non-nucleophilic base used in the present invention. 2,6-Di-tert-butylated pyridine also is useful as a base in the present method. TTBP is a preferred base because it is a white, non-hygroscopic, crystalline solid that is not readily sublimed under vacuum. However, the crystalline nature of TTBP renders it relatively insoluble in dichloromethane at −78° C., and, therefore, the reaction is performed at about −60° C. 2,6-Di-tert-butylated pyridine preferably is used as the base when a temperature lower than about −60° C. is desired or required.

A thioglycoside activated by the present activating system can be, for example, a pentose or hexose sugar, or a sialic acid; with a broad range of stereochemistry, including, but not limited to, xylose, rhamnose, glucose, galactose, mannose, glucosamine, and N-acetyl neuraminic acid.

The following illustrates a general reaction scheme of the present invention for solution glycosylation using a thioglycoside:

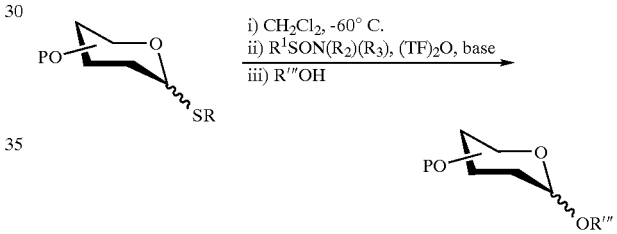

wherein P is a protecting group, typically a benzyl group (armed) or an acetyl or benzoyl group (disarmed);

R is alkyl or aryl, typically an ethyl or phenyl group;

R$^1$ is an aryl, heteroaryl, or C$_{1-6}$alkyl group, typically a phenyl group;

R$^2$ and R$^3$ are as defined above, with N(R$^2$)R$^3$ typically being piperidinyl, N(CH$_3$)$_2$, or N(C$_2$H$_5$)$_2$;

R'" OH is a primary, secondary, or tertiary alcohol; and base is a mild, sterically hindered base, such as, but not limited to, 2,6-di-tert-butylpyridine or 2,4,6-tri-tert-butylpyrimidine. In another embodiment, (R'")$_2$NH or (R'")NH$_2$ can be substituted for R'" OH.

Examples of forming glycosidic bonds using a thioglycoside activated by an N,N-dialkylsulfinamide and Tf$_2$O are set forth in the following Table 1. Table 1 illustrates the diversity and range of thioglycoside donors and acceptor alcohols (R'"OH) useful in the method of the present invention. Especially noteworthy is coupling of mannose, in the form of a β-mannoside, to a tertiary alcohol, as illustrated in Table 1, entry 2. Also of particular note are the double glycosylations of carbohydrate diols, illustrated in entries 14 and 15 of Table 1.

TABLE 1

Solution Phase Glycosylations

| Entry | Donor | Acceptor |
|---|---|---|
| 1 | Ph-benzylidene protected thioglycoside donor with OBn, BnO, SPh | Diacetone sugar with free OH |
| 2 | Ph-benzylidene protected thioglycoside donor with OBn, BnO, SPh | 1-adamantanol |
| 3 | Ph-benzylidene protected thioglycoside donor with BnO, BnO, SPh | Diacetone sugar with free OH |
| 4 | Ph-benzylidene protected thioglycoside donor with BnO, BnO, SPh | 1-adamantanol |
| 5 | Per-acetylated fucose thioglycoside (SPh, AcO, AcO, OAc) | Methyl 3,4,6-tri-O-acetyl-α-glucoside with free 2-OH |
| 6 | Per-acetylated fucose thioglycoside (SPh, AcO, AcO, OAc) | Threonine derivative (HO, NHCO₂CH₂Ph, Me, CO₂Me) |
| 7 | Per-benzoylated thioglycoside (OBz, BzO, BzO, BzO, SPh) with α/β mixture | Methyl 3,4,6-tri-O-acetyl-α-glucoside with free 2-OH |
| 8 | Per-benzoylated thioglycoside (OBz, BzO, BzO, SPh) | Diacetone sugar with free OH |

TABLE 1-continued
Solution Phase Glycosylations
| 9 | 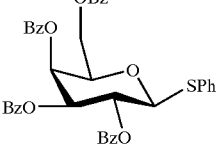 | 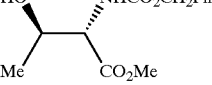 |
| --- | --- | --- |
| 10 | 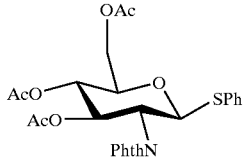 | 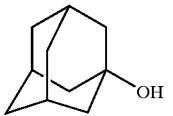 |
| 11 | 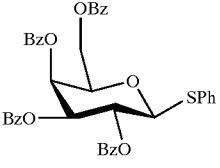 | 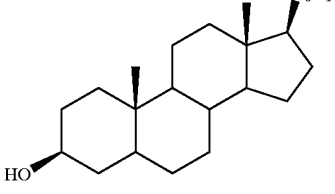 |
| 12 |  | 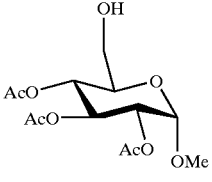 |
| 13 | 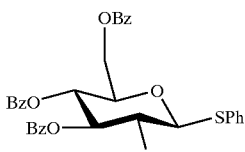 | 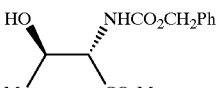 |
| 14 | 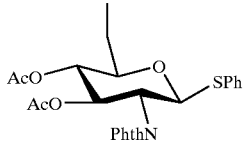 | 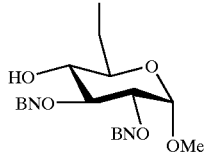 |
| 15 | 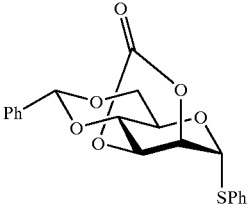 | 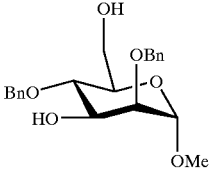 |

TABLE 1-continued

Solution Phase Glycosylations

| Entry | Product | Yield (%) |
|---|---|---|
| 1 | (structure) | 77 |
| 2 | (structure) | 88 |
| 3 | (structure) | 74 |
| 4 | (structure) | 72 |
| 5 | (structure) | 71 |
| 6 | (structure) | 77 |

TABLE 1-continued

Solution Phase Glycosylations

| # | Structure | Yield |
|---|---|---|
| 7 | (trisaccharide: BzO-protected sugar linked to AcO-protected sugar-OMe) | 80 |
| 8 | (disaccharide: BzO-protected pyranose linked to diisopropylidene furanose) | 72 |
| 9 | (BzO-protected sugar linked to threonine derivative with NHCO₂CH₂Ph and CO₂Me) | 72 |
| 10 | (AcO-protected PhthN sugar linked to adamantyl) | 74 |
| 11 | (BnO-protected sugar linked to cholestanyl, C₈H₁₇ side chain) | 70 |
| 12 | (disaccharide: BzO-protected linked to AcO-protected-OMe) | 70 |
| 13 | (BzO-protected sugar linked to threonine derivative with NHCO₂CH₂Ph and CO₂Me) | 71 |

TABLE 1-continued

Solution Phase Glycosylations

| | | |
|---|---|---|
| 14 | [structure] | 84 |
| 15 | [structure] | 65 |

Table 1 illustrates the effectiveness of the present activating system using phenyl thioglycosides as donors. However, ethyl thioglycosides are activated equally well as phenyl glycosides. It also has been found that a selenoglycoside can be activated by the N,N-dialkylsulfinamide/Tf$_2$O/optional base method of the present invention, as illustrated below:

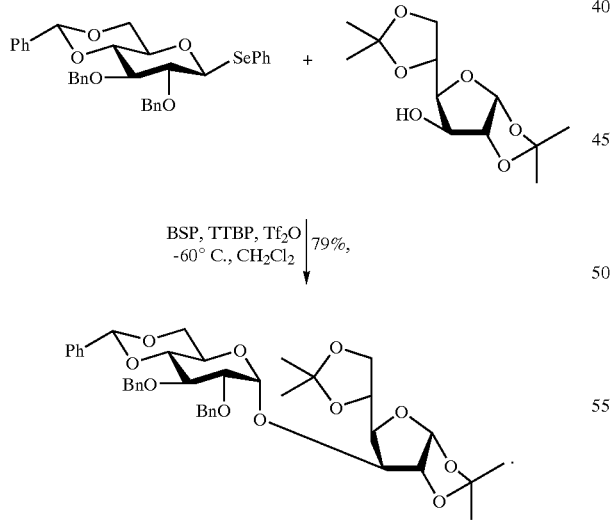

The selenoglycoside reaction was extremely α-selective (α:β>9:1). The differential reactivity of thioglycosides and selenoglycosides to the BSP/Tf$_2$O activating system is envisioned as providing a one-pot oligosaccharide synthesis.

An important feature of the present method is the double glycosylation of carbohydrate diols. One example illustrated below is coupling of a 4,6-glucopyranosyl diol (3) to the phthalimide protected glycosamine donor (4), which resulted in the isolation of the trisaccharide (5) in 85% yield.

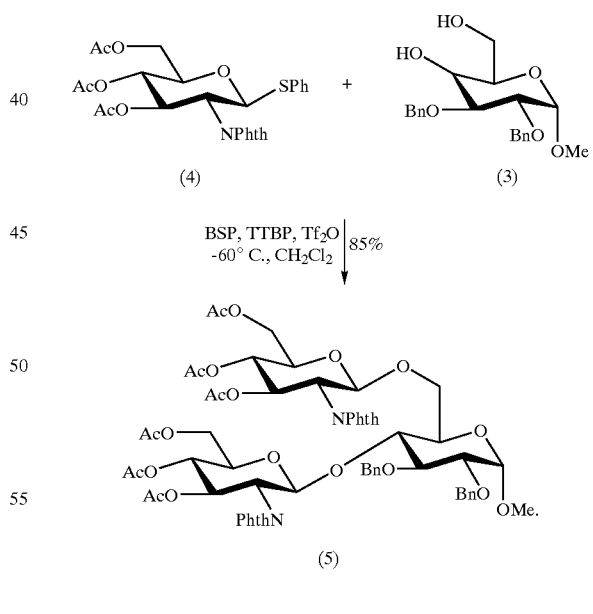

A second example is coupling of a mannopyranosyl diol (6) to a highly α-selective mannosyl donor (7) resulting in the formation of the mannotriose (8), as illustrated below. This particular example illustrates a synthesis of a protected version of the trisaccharide substrate of the mannose binding protein concanavalin A.

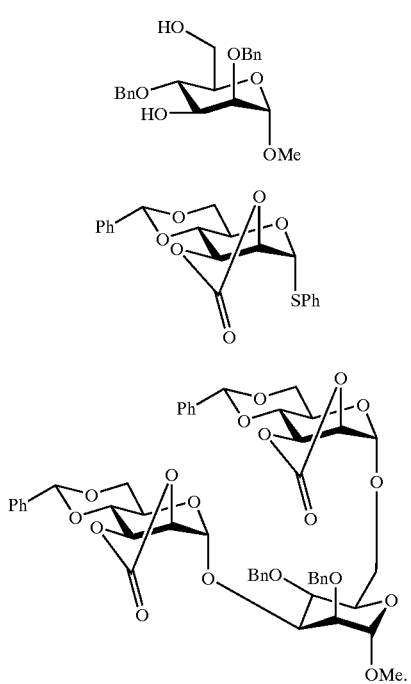

From the above examples, it has been shown that the present N,N-dialkylsulfinamide and Tf$_2$O activating system is considerably more potent than the MPBT/Tf$_2$O method. The N,N-dialkylsulfinamide and Tf$_2$O method activates a full range of armed and disarmed glycosyl donors, under a standard set of conditions. Accordingly, the present method differs from other methods of thioglycoside activation, particularly most other glycosylations methods that with few exceptions, require alternative conditions for arming and disarming protecting groups. The generalized reaction conditions provided by the present method facilitates use of the method by nonspecialists, and is of a benefit in the development of fully automated oligosaccharide synthesizers. It is also important that products of the present BSP/Tf$_2$O glycosylations are easier to purify than the prior MPBT glycosylations. The present invention generates fewer by-products and, because fewer reagents are required, separation of by-products is considerably easier.

General Method for the Preparation of Glycosides.

To a stirred solution containing a thioglycoside (0.185 mmol), 1-benzenesulfinyl piperidine (BSP, 0.185 mmol), TTBP (0.370 mmol), and activated 3 Å powdered sieves in CH$_2$Cl$_2$ (5 mL), at −60° C. under an argon atmosphere, was added Tf$_2$O (0.203 mmol). After five minutes, a solution of a glycosyl acceptor (0.277 mmol) in dichloromethane (2 mL) was added. The reaction mixture was stirred for two minutes at −60° C., then warmed to room temperature, filtered, washed with saturated aqueous sodium bicarbonate (NaHCO), followed by brine, dried over magnesium sulfate (MgSO$_4$) and concentrated under reduced pressure. The glycosides were isolated by chromatography on silica gel.

Preparation of Methyl 2,4-Di-O-benzyl-3-O-(2,3-O-carbonyl-4,6-O-benzylidene-α-D-mannopyranosyl)-6-O-(2,3-O-carbonyl-4,6-O-benzylidene-α-D-mannopyran-osyl)-α-D-mannoside (8)

To a stirred solution containing the thioglycoside (7) (D. Crich et al., *J. Org. Chem.*, 65, 1291–1297 (2000)) (0.140 g, 0.36 mmol), BSP (0.080 g. 0.38 mmol), TTBP (0.164 g. 0.66 mmol), and activated 3 Å powdered sieves in CH$_2$Cl$_2$ (5 mL), at −60° C. under an argon atmosphere, was added Tf$_2$O (0.064 mL, 0.39 mmol). After five minutes, a solution of the glycosyl acceptor (6) (0.062 g. 0.165 mmol) in CH$_2$Cl$_2$ (2 mL) was added. The reaction mixture then was warmed to room temperature, filtered, washed with saturated aqueous NaHCO$_3$, followed by brine, dried (MgSO$_4$), and concentrated under reduced pressure. The residue was purified by chromatography on silica gel (ethyl acetate:hexanes (1:1)) to yield compound (8) as a clear viscous oil (0.10 g, 65%): $[\alpha]^{20}_D$+11.7 (c 0.8); $^1$H NMR (C$_6$D$_6$) δ: 3.13 (3H, s), 3.37 and 3.44 (each 1H, t, J=10.5 Hz), 3.52 (1H, dd, J=8 and 10 Hz), 3.58–3.62 (2H, m), 3.65–3.68 (2H, m), 3.73–3.78 (2H, m), 3.87 (1H, dt, J=5 and 10 Hz), 4.06 (1H, d, J=7 Hz) 4.10 (1H, dd, J=5 and 10 Hz), 4.17 (1H, q, J=10 Hz), 4.20 (1H, dd, J=5 and 10 Hz), 4.25–4.28 (2H, m), 4.33 (1H, d, J=11.5 Hz), 4.39 and 4.43 (each 1H, t, J=7.5 Hz), 4.50 (1H, d, J=11.5 Hz), 4.63 (1H, d, J=11 Hz), 4.66 (1H, d, J=1.5 Hz), 4.70 (1H, d, J=11 Hz), 5.11 and 5.15 (each 1H, s), 7.24–7.63 (20H, m); $^{13}$C NMR δ: 55.6, 60.0, 60.3, 66.9, 68.9, 69.0, 72.3, 73, 75.1, 75.4, 75.5, 75.8, 76.8, 77.6, 78.2, 78.6, 78.9, 79.1, 97.0, 98.2, 98.3, 102.3, 102.4, 126.5, 126.6, 128.4, 128.8, 128.9, 129.1, 129.2, 129.8, 136.8, 136.9, 137.7, 137.8; HRMS calcd. for C$_{49}$H$_{50}$O$_{18}$Na [M+Na]$^+$: 949.2895, found: 949.2950.

The following are additional examples showing the usefulness of the present method. Unless otherwise stated, all $^1$H and $^{13}$C NMR spectra were recorded in CDCl$_3$ solution at 300 and 75 MHz, respectively. All specific rotations are for CHCl$_3$ solutions. All extracts were dried over MgSO$_4$.

Preparation of 1-O-(2,3-di-O-allyl-4,6-O-benzylidene-β-D-mannopyranosyl)-3-O-tert-butyldimethyl-silyl-2,3-O-ethylidene-D-erythitol (9) from sulfide (10)

To a mixture of the azeotropically dried thioglycoside (10) (0.080 g, 0.19 mmol), BSP (0.040 g, 0.19 mmol), TTBP (0.095 g, 0.38 mmol), and 3 Å powdered molecular sieves in dry CH$_2$Cl$_2$ (3.0 mL) was added, under argon, Tf$_2$O (0.035 mL, 0.21 mmol) at −60° C. The reaction mixture was stirred for five minutes, then acceptor (11) was added (0.080 g, 0.21 mmol) in CH$_2$Cl$_2$ (2.0 mL). The dry-ice bath was removed, and the reaction mixture was warmed slowly to room temperature, then quenched with saturated NaHCO$_3$ solution (3 mL), washed with water (1×20 mL), and brine (1×20 mL). The organic layer was dried and concentrated under vacuum. Flash column chromatography on silica gel (eluent:ethyl acetate (EtOAc)/-hexanes=2:8) yielded compound (9) (0.075 g, 66%), identical in all respects to a sample isolated earlier.

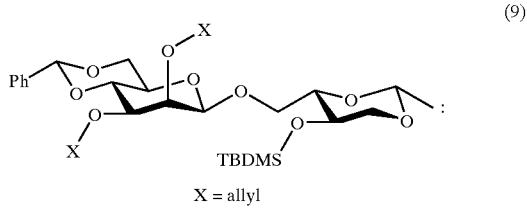

X = allyl

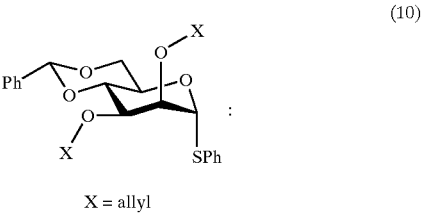

X = allyl

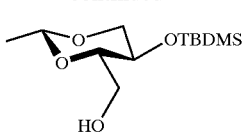

Preparation of 4-tert-butyldiphenylsiloxy-2Z-buten-1-yl 4,6-O-benzylidene-2,3-di-O-p-bromobenzyl-β-D-mannopyranoside (14) from thioglycoside (12)

To a mixture of azeotropically dried sulfide (12) (0.500 g, 0.72 mmol), BSP (0.150 g, 0.72 mmol), TTBP (0.350 g, 1.41 mmol), and powdered molecular sieves in dry CH$_2$Cl$_2$ (3.0 mL) was added Tf$_2$O (0.130 mL, 0.790 mmol) at −60° C. under argon. The reaction mixture was stirred for five minutes before acceptor (13) (0.470 g, 1.44 mmol) was added in CH$_2$Cl$_2$ (2.0 mL). The dry-ice bath was removed, and the reaction mixture was warmed to room temperature, quenched with saturated NaHCO$_3$ solution (5.0 mL), washed with water (1×20 mL), and brine (1×20 mL). The organic layer was dried and concentrated under vacuum. Flash column chromatography on silica gel (eluent:EtOAc/hexanes=2:8) yielded compounds (14α) (0.040 g, 6%) and (14β) (0.550 g, 84%). The β-anomer was identical to the above-prepared sample. The α-anomer had $[\alpha]^{23}_D$=+13.1° (c 6.7); $^1$H NMR δ: 7.75 (m, 4H), 7.55–7.45 (m, 15H), 7.22 (d, J=7.0 Hz, 2H), 7.20 (d, J=70 Hz, 2H), 5.82–5.75 (m, 1H), 5.61 (s, 1H), 5.53–5.44 (m, 1H), 4.70–4.52 (m, 5H), 4.25–4.12 (m, 4H), 4.03 (dd, J=5.7, 13.2 Hz, 1H), 3.95–3.68 (m, 5H), 1.06 (s, 9H); $^{13}$C NMR δ: 137.8, 137.2, 135.7, 133.1, 131.9, 131.7, 131.6, 131.5, 129.9, 129.8, 129.4, 129.2, 129.0, 128.4, 128.0, 127.9 126.2, 125.8, 121.8, 121.5, 101.6, 98.5, 79.3, 77.6, 77.2, 77.0, 76.8, 76.6, 73.0, 72.6, 68.8, 64.3, 63.2, 60.4, 26.9, 19.28.

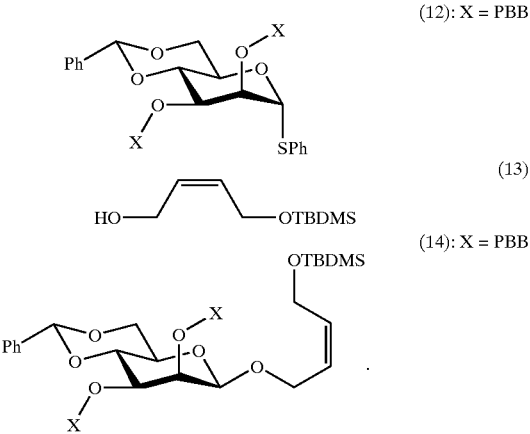

Preparation of Acceptor (11)

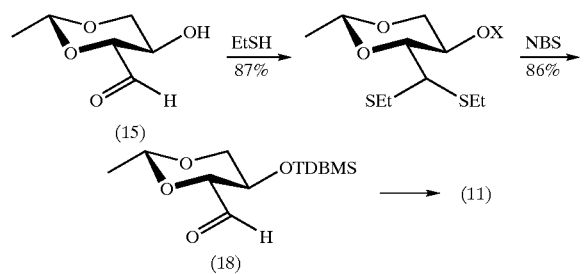

2,4-O-Ethylidene-D-erythrose diethyl thioacetal (16)

A cold solution of ZnCl$_2$ (8 g, 58.7 mmol) in ethanethiol (12.6 mL, 170.2 mmol) and dry THF (25 mL) was added to a solution of 2,4-O-ethylidene-D-erythrose (15) (8.3 g, 56.8 mmol) at 0° C. under argon. The reaction mixture was stirred for 2 hours at 0° C., diluted with diethyl ether (200 mL), washed with 2M HCl, water, and brine, dried, filtered, and evaporated under reduced pressure. The resulting oil was purified by column-chromatography (eluent: ether/pentane 2:3) to provide compound (16) as a colorless oil (12.42 g, 87%): $[\alpha]^{22}_D$=−25.4° (c 0.9); $^1$H NMR δ: 4.60 (q, J=5.1 Hz, 1H), 4.03 (m, 2H), 3.92 (m, 1H), 3.64 (dd, J=3.5, 9.0 Hz, 1H), 3.32 (t, J=10.4 Hz, 1H), 2.91 (d, 1H), 2.67 (m, 4H), 1.25 (d, 3H), 1.20 (t, J=7.4 Hz, 3H), 1.19 (t, J=7.4 Hz, 3H); $^{13}$C NMR δ: 99.3, 84.8, 70.3, 63.7, 52.0, 25.5, 25.4, 20.5, 14.5 (2 C's); HRMS calcd. for C$_{10}$H$_{20}$O$_2$S$_2$ [M$^+$]: 252.0854. Found: 252.0855.

2,4-O-Ethylidene-3-O-tert-butyldimethylsilyl-D-erythose diethyl thioacetal (17)

To a solution of compound (16) (10.10 g, 40.1 mmol) in dry dimethylformamide (DMF) (20 mL), imidazole (7.4 g, 108.7 mmol) and tert-butylidimethylsilyl chloride (8.16 g, 54.1 mmol) were added. The solution was maintained at 46° C. for 3 hours and subsequently stirred at room temperature for 12 hours. The solution then was diluted with ether, washed with water, 2M HCl, saturated NaHCO$_3$, water, and brine, dried, filtered, and evaporated under reduced pressure. Purification was achieved by column chromatography (eluent:ether/pentane 1:24) and compound (17) was isolated as an oil (12.39 g, 96%): $[\alpha]^{22}_D$=−12.4° (c 0.0); $^1$H NMR δ: 4.62 (q, J=5.0 Hz, 1H), 4.04 (d, J=1.6 Hz, 1H), 3.96 (m, 2H), 3.70 (b d, J=8.5 Hz, 1H), 3.30 (m, 1H), 2.67 (m, 4H), 1.28 (d, 3H), 1.22 (t, J=7.3 Hz, 3H), 1.20 (t, J=7.5 Hz, 3H), 0.81 (s, 9H), 0.07 (s, 3H), 0.03 (s, 3H); $^{13}$C NMR δ: 99.3, 86.6, 71.0, 63.8, 51.2, 25.7, 25.5, 24.9, 20.6, 17.9, 14.7, 14.4, −4.9; Anal. Calcd. for C$_{16}$H$_{34}$O$_3$S$_2$Si: C, 52.41; H, 9.35. Found: C, 52.73; H, 9.43.

2,4-O-Ethylidene-3-O-tert-butyldimethylsilyl-D-erythrose (18)

A solution of compound (12) (3.77 g, 10.3 mmol) in acetonitrile (5 mL) was added dropwise to a solution of N-bromosuccinimide (NBS) (11 g, 61.8 mmol) in 80% aqueous acetonitrile at −20° C. The reaction mixture was stirred for 30 minutes at −20° C., diluted with chloroform, washed twice each with saturated Na$_2$SO$_3$, 2 M HCl, NaHCO$_3$, and water, dried, filtered, and evaporated under reduced pressure. The oily product (18) was dried at 60° C. in high vacuum for 3 hours (2.29 g, 86%) and used without further purification: $[\alpha]^{22}_D$=−35.9° (c 0.6 CHCl$_3$); IR: 1743 cm$^{−1}$ (CHCl$_3$); $^1$H NMR δ: 9.68 (d, J=1.1 Hz, 1H), 4.69 (q, J=5.1 Hz, 1H), 4.05 (dd, J=5.0, 10.8 Hz, 1H), 3.90 (dd, J=1.1, 9.5 Hz, 1H), 3.77 (m, 1H), 3.41 (dd, J=9.7, 10.7 Hz, 1H), 1.35 (d, J=5.1 Hz, 3H), 0.83 (s, 9H), 0.03 (s, 3H), 0.02 (s, 3H); $^{13}$C NMR δ: 197.3, 98.8, 84.5, 71.3, 62.7, 25.8, 20.4, 17.9, −4.3, −4.9.

2,4-O-Ethylidene-3-O-tert-butyldimethylsilyl-D-erythritol (11)

To a stirred solution of compound (18) (1.10 g, 4.2 mmol) in CH$_2$Cl$_2$ (20 mL) was added sodium borohydride (0.16 g, 12.6 mmol) in ethanol (5 mL). The reaction mixture was stirred for 2 hours at room temperature, then quenched with water (2 mL), diluted with CH$_2$Cl$_2$ (30 mL), washed with saturated NaHCO₃ solution (1×20 mL), water (1×20 mL), and brine (1×20 mL). The organic layer was dried, filtered, concentrated in vacuo, and purified by flash column chromatography on silica gel (eluent: EtOAc/hexanes=1:1) to give compound (11) (0.90 g, 80%): $[\alpha]^{23}{}_D$=−39.0° (c 1.9); $^1$H NMR δ: 4.69 (q, J=5.1 Hz, 1H), 3.99 (dd, J=5.1, 10.8 Hz, 1H), 3.81 (b d, J=11.7 Hz, 1H), 3.69–3.61 (m, 2H), 3.45–3.38 (m, 1H), 3.34 (t, J=10.5 Hz, 1H), 2.04 (b t, 1H), 1.31 (d, J=5.4 Hz 3H), 0.84 (s, 9H), 0.06 (s, 3H), 0.04 (s, 3H); $^{13}$C NMR δ: 98.9, 81.8, 71.1, 62.5, 62.0, 25.7, 20.6, 18.0, −4.3, −4.9. Anal. Calcd. for $C_{12}H_{26}O_4Si$: C, 54.92; H, 9.99. Found:. C, 55.51; H, 9.78.

Preparation of Sulfide (10)
S-Phenyl 2,3-di-O-allyl-4,6-O-benzylidene-1-thia-α-D-mannopyranoside (10)

A flask containing diol (19) (1.0 g, 2.76 mmol) was purged with nitrogen and charged with DMF (20 mL) and sodium hydride (NaH) (0.24 g, 10.08 mmol, 60% dispersion in oil), previously washed with hexane (3×10 mL), was added. After stirring for 20 minutes, the reaction mixture was cooled to 0° C. followed by the addition of allyl bromide (1.85 mL, 6.07 mmol). The reaction mixture was stirred for 3 hours at room temperature, then quenched by the dropwise addition of methanol (1.0 mL) and saturated NaHCO₃ solution (10 mL), diluted with EtOAc, and washed with water (1×20 mL) and brine (1×20 mL). The organic layer was dried, filtered, concentrated in vacuo and purified by flash column chromatography on silica gel (eluent:EtOAc/hexanes 1:9) to provide compound (10) (1.2 g 98%): $[\alpha]^{23}{}_D$=+139.7° (c 2.4); $^1$H NMR δ: 7.54–7.28 (m, 10H), 6.00–5.88 (m, 2H), 5.63 (s, 1H), 5.57 (s, 1H), 5.37 (b d, J=17 Hz, 1H), 5.34 (b d, J=17.2 Hz, 1H), 5.22 (d, J=10.5 Hz, 2H), 4.39–4.05 (m, 9H), 3.92 (d, J=3 Hz, 1H), 3.88 (m, 2H); $^{13}$C NMR δ: 137.7, 134.9, 131.5, 129.3, 129.0, 128.3, 127.7, 126.2, 118.1, 117.1, 101.7, 87.4, 79.3, 78.3, 75.9, 72.6, 72.2, 68.6, 65z4, 21.2, 11.8, 10.0; ESI HRMS Calcd. for $C_{25}H_{28}O_5S$ [M+Na]⁺: 463.1555. Found: 463.1565.

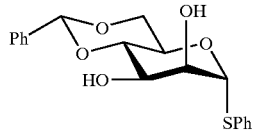

(19)

Preparation of Thioglycoside (12)
S-Phenyl 2,3-di-O-p-bromobenzyl-4,6-O-benzylidene-1-thia-α-D-mannopyranoside (12)

Compound (12) was prepared in quantitative yield, as a white crystalline solid from diol (19) and p-bromobenzyl bromide according to the protocol described for the allyl analog (10): $[\alpha]^{23}{}_D$+66.7° (c 2.3); mp=113–115° C.; $^1$H NMR δ: 7.51–7.18 (m, 18H), 5.64 (s, 1H), 5.50 (d, J=1.5 Hz, 1H), 4.77 (d, J=12.3 Hz, 1H), 4.7–4.57 (m, 3H), 4.3–4.21 (m, 3H), 4.01 (m, 1H), 3.97–3.86 (m, 2H); $^{13}$C NMR δ: 137.6, 137.4, 136.8, 131.8, 131.7, 131.6, 129,8, 129.4, 129.3, 129.1, 128.4, 127.9, 126.2, 122.0, 121.7, 101.7, 87.1, 79.2, 78.5, 76.4, 72.6, 72.4, 68.6; 65.5; Calcd. for $C_{33}H_{30}Br_2O_5S$: C, 56.75; H, 4.33. Found: 56.37; H, 4.26; ESI HRMS Calcd. for $C_{33}H_{30}Br_2O_5S$ [M+Na]⁺: 719.0078. Found: 719.006.

Compound 13 was prepared by the method W. R. Rousch et al., *J. Org. Chem.*, 56, 1636 (1991).

1-[4-(4-Nitrophenyl)butyl 4,6-O-Benzylidene-2-pivaloyl-3-O-(2,3-O-isopropylidene-4-O-(tert-butyldimethylsilyl)-α-L-rhamnopyranosyl)-β-D-galactopyranoside (22)

By the standard BSP protocol disclosed above, coupling of thioglycoside (19) (0.258 g, 0.63 mmol) with acceptor (21) (0.197 g, 0.37 mmol) provide disaccharide (22) (0.198 g, 0.24 mmol) in 64% yield as a white solid: mp 128±1° C.; $[\alpha]_D$−25.3° (c, 0.1); $^1$H NMR (500 MHz) δ: 8.10 (d, J=8.4 Hz, 2H), 7.20–7.56 (m, 7H), 5.52 (s, 1H, $^1J_{CH}$=166.1 Hz), 5.27 (dd, J=8.1, 10.4 Hz, 1H), 5.02 (s, 1H), 4.46 (d, J=8.1 Hz, 1H), 4.32–4.38 (m, 2H), 4.07 (dd, J=1.4, 12.3 Hz, 1H), 3.98–4.04 (m, 2H), 3.88–3.98 (m, 1H), 3.83 (dd, J=6.4, 10.0 Hz, 1H), 3.73 (dd, J=3.6, 10.5 Hz, 1H), 3.42–3.54 (m, 2H), 3.22–3.32 (m, 1H), 2.64–2.78 (m, 2H), 1.52–1.82 (m, 4H), 1.48 (s, 3H), 1.25 (s, 3H), 1.20 (d, J=3.9 Hz, 3H), 1.18 (s, 9H), 0.8 (s 9H) 0.11 (s, 3H), 0.04 (s, 3H); $^{13}$C NMR (125 MHz) δ: 177.0, 150.8, 146.7, 137.9, 129.6, 129.4, 128.6, 126.6, 124.0, 109.2, 101.7, 101.5, 100.8, 80.2, 79.0, 77.7, 76.3, 76.2, 76.1, 69.8, 69.6, 68.8, 67.0, 66.9, 39.1, 35.9, 29.4, 28.4, 27.9, 27.5, 26.6, 26.2, 18.4, 18.3, −3.5, −4.6. Anal. Calcd. for $C_{43}H_{63}O_{13}NSi$: C, 62.22; H, 7.65. Found: C: 62.05; H, 7.57.

1-[4-(4-Nitrophenyl)butyl 4,6-O-Benzylidene-2-pivaloyl-3-O-[4-O-(2,3-O-dibenzyl-4,6-O-benzylidene-β-D-mannopyranosyl)-2,3-O-carbonyl-α-L-rhamnopyranosyl]-β-D-galactopyranoside (24β) and 1-[4-(4-Nitro-phenylbutyl 4,6-O-Benzylidene-2-pivaloyl-3-O-[4-O-(2,3-di-O-benzyl-4,6-O-benzylidene-α-D-mannopyranosyl)-2,3-O-carbonyl-α-L-rhamnopyranosyl]-β-D-galactopyranoside (24α)

Coupling of compound (12) (0.067 g, 0.124 mmol) with compound (23) (0.043 g, 0.0 62 mmol) by the standard BSP protocol disclosed above provided compound (24βα) (0.064 g, 0.056 mmol) in 90% yield with a β:α ratio of 2:1 as determined from the $^1$H NMR spectrum of the α:β mixture after column chromatography. Part of the β:α mixture was further purified by preparative TLC on silica gel (eluent:EtOAc/hexane 1/2) to give samples of the two pure isomers. The pure β isomer was a white solid: mp 108±10° C.; $[\alpha]_D$−16.3° (c, 1.7): $^1$H NMR δ: 8.10 (d., J=8.7 Hz, 2H), 7.18–7.56 (m, 22H), 5.58 (s, 1H), 5.53 (s, 1H), 5.34 (dd, J=7.6, 10.0 Hz, 1H), 5.10 (s, 1H), 4.64–4.76 (m, 4H), 4.58 (d, J=12.6 Hz, 1H), 4.47 (d, J=8.1 Hz, 1H), 4.42 (d, J=7.5 Hz, 1H), 4.24–4.38 (m, 4H), 4.06–4.20 (m, 2H), 3.82–4.00 (m, 5H), 3.78 (dd, J=3.4, 10.0 Hz, 1H), 3.48–3.62 (m, 3H), 3.48 (s, 1H), 3.26–3.36 (m, 1H), 2.68–2.78 (m, 2H), 1.56–1.80 (m, 4H), 1.30 (d, J=6.3 Hz, 3H), 1.17 (s, 9H); $^{13}$C NMR δ: 176.9, 153.0, 150.4, 138.0, 137.6, 137.4, 129.5, 129.3 129.0, 128.9, 128.5, 128.3, 128.2, 127.9, 127.8, 127.7, 126.4, 126.3, 126.2, 123.7, 101.7, 101.6, 101.1, 100.7, 98.2, 80.7, 78.8, 78.6, 78.2, 78.0, 77.6, 76.7, 75.8, 75.5, 74.9, 72.7, 69.4, 69.2, 68.8, 68.4, 67.7, 66.3, 64.2, 39.0, 35.6, 29.2, 27.6, 27.3, 17.7; ESI HRMS calcd. for $C_{62}H_{69}O_{19}N_1Na$ [M+Na]⁺ m/e 1154.4361, found m/e 1154.4292. The pure α isomer was a glass: $[\alpha]_D$+8.3° (c, 0.1); $^1$H NMR δ: 8.10 (d, J=8.8 Hz, 2H), 7.20–7.58 (m, 22H), 5.63 (s, 1H), 5.47 (s, 1H), 5.26 (dd, J=8.0, 10.0 Hz, 1H), 4.90 (s, 1H), 4.80–4.92 (m, 2H), 4.56–4.72 (m, 4H), 4.38–4.48 (m, 3H), 4.33 (d, J=11.7 Hz, 1H), 4.20–4.28 (m, 2H), 4.08 (d, J=11.7 Hz, 1H), 3.64–3.98 (m, 8H), 3.40–3.52 (m, 2H), 3.28 (dd, J=7.3, 10.4 Hz, 1H), 2.64–2.78 (m, 2H), 1.56–1.80 (m, 4H), 1.15 (s, 9H), 0.86. (d, J=6.3 Hz, 3H); $^{13}$C NMR δ: 176.8, 152.9, 150.3, 137.9, 137.8, 137.4, 129.4, 129.3, 128.9, 128.6, 128,5, 128.4, 128.3, 128.2, 128.1, 127.7, 127.6, 126.3, 126.2, 123.7, 101.5, 101.4, 101.1, 101.0, 97.9, 80.4, 78.9, 78.6, 77.4, 77.3, 76.6, 76.5, 75.5, 75.4, 74.1, 73.7, 69.3, 68.8, 68.4, 66.3, 64.9, 64.5, 38.9, 35.6, 29.2, 27.6, 27.3, 17.0; ESI HRMS calcd. for $C_{62}H_{69}O_{19}N_1Na$ [M+Na]⁺ m/e 1154.4361, found m/e 1154.4323.

1-[4-(4-Nitrophenyl)butyl 4,6-O-Benzylidene-2-pivaloyl-3-O-[4-O-(4,6-O-benzylidene-2,3-di-O-(p-methoxybenzyl)-β-D-mannopyranosyl)-2,3-O-isopropyl-idene-α-L-rhamnopyranosyl]-β-D-galactopyranoside (25β) and 1-[4-

(4-Nitrophenyl)butyl 4,6-O-Benzylidene-2-pivaloyl-3-O-[4-O-(4,6-O-benzylidene-2,3-di-O-(p-methoxybenzyl)-α-D-mannopyranosyl)-2,3-O-iso-propylidene-α-L-rhamnopyranosyl]-β-D-galactopyranoside (25α)

By the standard BSP protocol, coupling of compound 26 (0.234 g, 0.39 mmol) with compound 27 (0.136 g, 0.19 mmol) gave the trisaccharide 25 (0.212 g, 0.18 mmol, α:β=1:9.6) in 92% yield. The pure β-isomer (0.163 g, 0.14 mmol) was obtained by column chromatography on silica gel (eluent:EtOAc/-hexane 1/3) in 71% yield as white foam, and an α:β=1:1.4) was obtained in 21% yield at the same time. A portion of this mixture was purified by preparative TLC on silica gel (eluent:EtOAc/hexane=1/3) to yield pure α-anomer. β-isomer: [α]$_D$31 19.0° (c, 0.2); $^1$H NMR (500 MHz) δ: 8.10 (d, J=8.7 Hz, 2H), 7.16–7.58 (m, 16H), 6.84 (d, J=8.6 Hz, 2H), 6.78 (d, J=8.6 Hz, 2H), 5.58 (s, 1H), 5.54 (s, 1H), 5.31 (dd, J=8.1, 9.8 Hz, 1H), 5.04 (s, 1H), 4.90 (s, 1H, $^1J_{CH}$ 160.7 Hz), 4.70 (d, J=11.7 Hz, 1H), 4.55 (d, J=11.7 Hz, 1H), 4.40–4.52 (m, 3H), 4.28–4.38 (m, 2H), 4.20 (dd, J=5.7, 10.2 Hz, 1H), 4.02–4.18 (m, 3H), 3.84–4.02 (m, 5H), 3.79 (s, 3H), 3.77 (s, 3H), 3.72–3.80 (m, 1H), 3.44–3.62 (m, 4H), 3.20–3.30 (m, 1H), 2.68–2.80 (m, 2H), 1.56–1.80 (m, 4H), 1.47 (s, 3H), 1.30 (d, J=6.2 Hz, 3H), 1.27 (s, 3H), 1.19 (s, 9H); $^{13}$C NMR (125 MHz) δ: 177.1, 159.6, 159.5, 150.7, 146.7, 138.0, 137.9, 130.8, 130.7, 130.6, 129.7, 129.6, 129.5, 129.4, 129.2, 128.6, 128.5, 126.7, 126.4 124.0, 114.2, 114.0, 113.8, 109.6, 101.9, 101.7, 101.5, 100.7, 80.5, 78.9, 78.4, 77.9, 77.8, 77.6, 77.3, 76.5, 76.1, 75.6, 74.7, 72.0, 69.8, 69.5, 69.0, 68.0, 66.8, 65.4, 60.8, 55.7, 55.6, 39.2, 35.8, 29.4, 28.1, 27.9, 27.5, 26.6, 18.2, 14.6; ESI HRMS calcd. for C$_{66}$H$_{79}$O$_{20}$N$_1$Na [M+Na]$^+$ m/e 1228.5093. Found m/e 1228.5032. The α-anomer was a glass: [α]$_D$+48.4° (c, 1.6); $^1$H NMR (500 MHz) δ: 8.13 (d, J=8.7 Hz, 2H), 7.25–7.55 (m, 16H), 6.87 (d, J=8.6 Hz, 2H), 6.82 (d, J=8.6 Hz, 2H), 5.65 (s, 1H), 5.53 (s, 1H), 5.32 (dd, J=8.0, 10.0 Hz, 1H), 5.03 (s, 1H), 4.80 (d, J=11.0 Hz, 2H), 4.77 (d, J=12.5 Hz, 1H), 4.65 (d, J=1.0 Hz, 1H), 4.60 (d, J=11.5 Hz, 1H), 4.59 (d, J=12.5 Hz, 1H), 4.48 (d, J=8.0 Hz, 1H), 4.36 (dd, J=1.2, 12.2 Hz, 1H), 4.18–4.26 (m, 2H), 4.00–4.14 (m, 3H), 3.92–3.98 (m, 1H), 3.90 (dd, J=3.5, 10.5 Hz, 1H), 3.82 (s, 3H), 3.78 (s, 3H), 3.75 (dd, J=3.5, 10.5 Hz, 1H), 3.71 (dd, J=1.0, 3.0 Hz, 1H), 3.46–3.52 (m, 2H), 3.21 (dd, J=7.5, 10.0 Hz, 1H), 2.70–2.80 (m, 2H), 1.50–1.75 (m, 4H), 1.48 (s, 3H), 1.27 (s, 3H), 1.17 (s, 9H), 0.88 (d, J=6.3 Hz, 3H); $^{13}$C NMR (125 MHz) δ: 177.1, 159.8, 150.7, 146.7, 137.9, 131.3, 130.4, 129.6, 129.5, 129.4, 129.2, 128.6, 128.5, 126.6, 124.0, 114.2, 114.1, 109.4, 101.8, 101.5, 100.9, 100.5, 80.5, 80.2, 79.6, 76.7, 76.6, 76.3, 76.1, 73.7, 73.6, 69.8, 69.0, 66.8, 65.9, 64.4, 55.7, 39.2, 35.9, 29.4, 28.4, 27.9, 27.5, 26.6, 17.4; ESI HRMS calcd. for C$_{66}$H$_{79}$O$_{20}$N$_1$Na [M+Na]$^+$ m/e 1228.5093, found m/e 1228.5031.

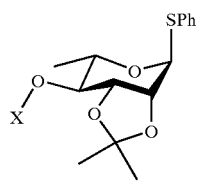

19 : X = TBDMS

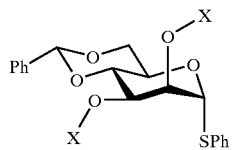

20: X = Bn
26: X = PMB

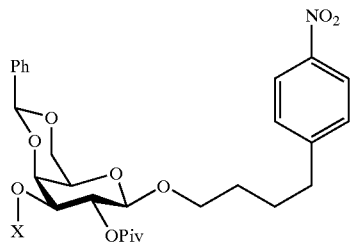

21: X = H

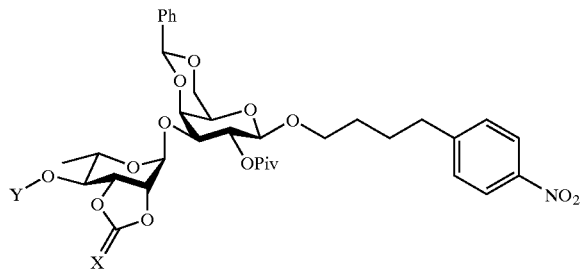

22: X = Me$_2$, Y = TBDMS
23: X = O
27: X = Me$_2$

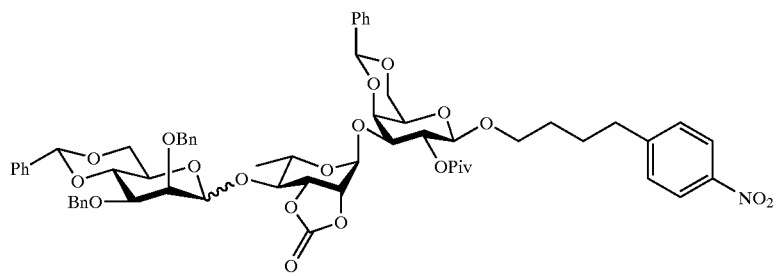

24

-continued

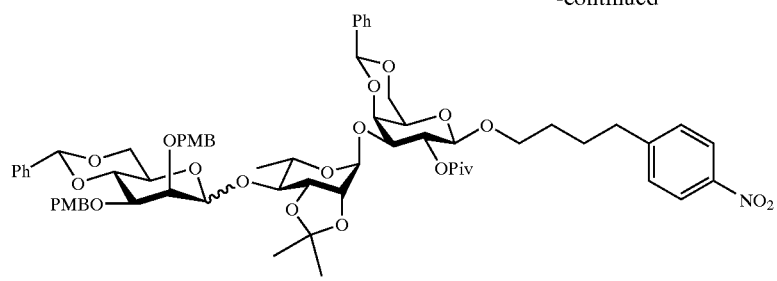

25: X = Piv

Solid-phase synthesis focuses on chemical reactions of substrates attached to solid supports (e.g., polystyrene, polyethylene glycol, cellulose, or controlled-pore glass) including methods for attachment and detachment from the supports. Solid-phase synthesis is of particular interest in the field of combinatorial and parallel synthesis.

The following illustrates a general reaction scheme for solid phase glycosylation using a thioglycoside:

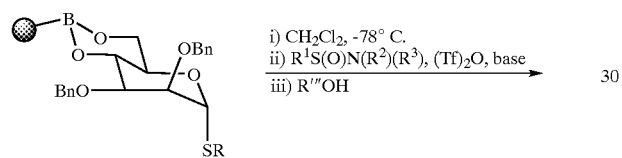

i) $CH_2Cl_2$, -78° C.
ii) $R^1S(O)N(R^2)(R^3)$, $(Tf)_2O$, base
iii) R'''OH

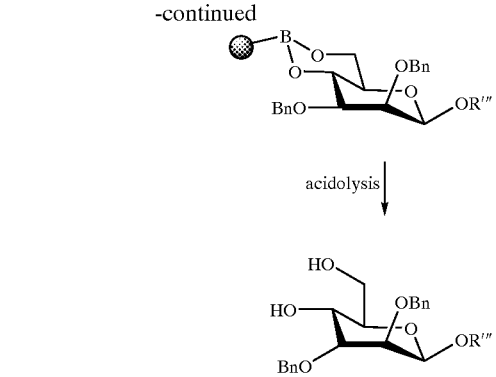

R through $R^3$, R''', and base are defined as for the solution phase system, and the polymer (●) is a crosslinked polystyrene resin, for example

TABLE 2

Polymer Supported Glycosylations

| Entry | Donor | Acceptor | Product | Yield (%) |
|---|---|---|---|---|
| 1 | | | | 82 |
| 2 | | | | 76 |

TABLE 2-continued

Polymer Supported Glycosylations

| Entry | Donor | Acceptor | Product | Yield (%) |
|---|---|---|---|---|
| 3 | (structure with polymer bead, B, O, OBn, BnO, SPh) | (structure with OH, AcO, AcO, AcO, OMe) | (disaccharide structure with HO, OBn, BnO, AcO, AcO, AcO, OMe) | 75 |

Polymer-supported synthesis of oligosaccharides is a rapidly emerging field, with successes using an automated synthesizer reported in O. J. Plante, *Science*, 291, 1523–1527 (2001). Nevertheless, the development of a truly versatile system for the automated, supported synthesis of oligosaccharides requires that methods for the highly diastereoselective synthesis of all classes of glycosidic bond be transposed to the solid phase. At the present time, the art still has not achieved that goal, with several classes of glycosidic bonds still presenting a considerable challenge even in solution. The present invention illustrates the first successful polymer-supported synthesis of the difficult β-mannopyranoside-type glycosidic bond.

In particular, the linkage of S-phenyl 2,3-di-O-benzyl-β-D-thiomannopyranoside to a crosslinked polystyrene support, in the form of its 4,6-O-polystyrylborinate ester, is disclosed. Activation of the polymer-supported mannosyl donor is achieved by at −60° C. in CH$_2$Cl$_2$ in the presence of 2,4,6-tri-tert-butylpyrimidine by a combination of BSP and Tf$_2$O. Addition of the donor alcohol at −60° C., followed by warming to room temperature, and subsequent cleavage from the resin by gentle heating in aqueous acetone yields anomerically pure 2,3-di-O-benzyl-β-D-mannopyranosides in excellent yield. Successful, diastereoselective coupling has been demonstrated with a range of primary secondary and tertiary glycosyl acceptors including typical carbohydrates and threonine derivatives.

The β-mannosides have long been recognized as one of the more important and challenging classes of glycosidic bonds. Accordingly, substantial effort has been spent on developing methods for their synthesis culminating in several successful strategies. These methods largely are indirect and consequently less than ideal for solid supported synthesis because of the extra steps that are required. The only method transferred to the solid phase to date is an adaptation of the intramolecular aglycon method which, by its very nature, results in cleavage from the resin concomitant with formation of the β-mannoside linkage (Y. Ito et al., *J. Am. Chem. Soc.*, 119, 5562–5566 (1997)).

In contrast to both the use of polystyrylboronic acid as a protecting group for carbohydrate diols (J. M. Fréchet et al., *J. Am. Chem. Soc.*, 101, 432–436 (1979)) and an extension thereof to the immobilization of thioglucoside 4,6-diols and the use of bound donors in coupling reactions (G. Belogi et al., *Tetrahedron Lett.*, 41, 6965–6968 (2000); G. Belogi et al., *Tetrahedron Lett.*, 41, 6969–6972 (2000)), phenylboronic acid derivatives were investigated. In order to determine whether the 4,6-O-phenylboronate ester exhibited the same torsionally disarming properties as the benzylidene group, diol (28) was condensed with phenylboronic acid to give compound (29). Compounds (29) were activated in dichloromethane at −60° C. in the presence of TTBP with BSP, and then coupled to 1-adamantanol to give the crude β-mannoside (30). Subjecting the residue to silica gel chromatography removed the phenylboronate ester to provide diol (31) in 72% yield The anomeric stereochemistry of diol (31) was confirmed by the $^1J_{CH}$ coupling constant (K. Bock et al., *Chem. Soc., Perkin Trans.* 2, 293–297 (1974)) of 152 Hz as well as by conversion of diol (31) into its known 4,6-O-benzylidine derivative (D. Crich et al., *Tetrahedron*, 54, 8321–8348 (1998)), with which it was identical.

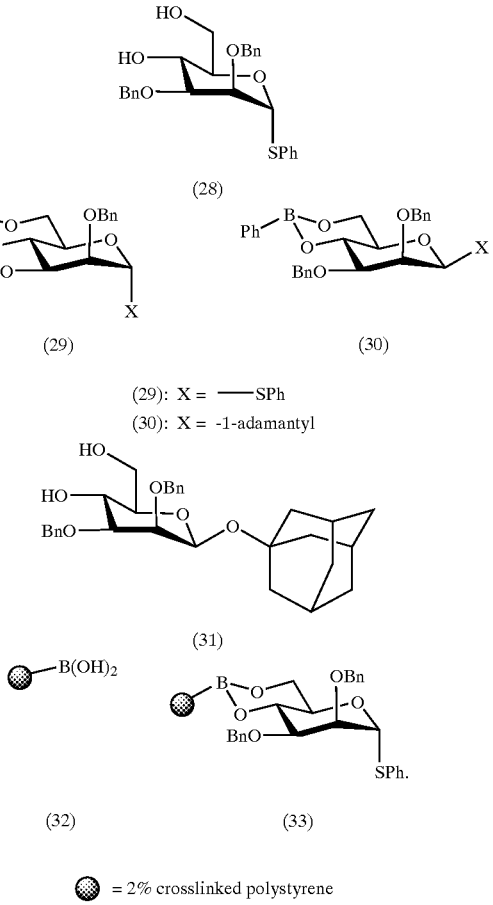

(29): X = ——SPh
(30): X = -1-adamantyl

● = 2% crosslinked polystyrene

The viability of the 4,6-O-phenylboronates as torsionally disarming protecting groups was thus established, and with the polymer-supported variant was tested. Accordingly, diol (28) was heated in pyridine with polystyrylboronic acid (32) (J. M. J. Fréchet et al., *J. Am. Chem. Soc.*, 101, 432–346 (1979); J. M. J. Fréchet et al., *J. Org. Chem.*, 41, 3877–3882 (1976)) to give the bound donor (33) with a loading of about 1 mmol/g as determined by the amount of diol (28) liberated on cleavage.

Activation of the bound thioglycoside (33) was achieved by stirring in $CH_2Cl_2$ with BSP at −60° C. in the presence of TTBP and $Tf_2O$ for 20 minutes, followed by addition of the acceptor alcohol, warming to room temperature and quenching. After removal of the excess reagents, alcohol, and by-products, the coupled β-mannosides (33) were released from the resin by heating in aqueous acetone for 1 hour to give the 4,6-diols (35).

The various β-mannosides prepared by this procedure are summarized in Table 3. The yields and selectivities summarized in Table 3 are unexpected.

TABLE 3

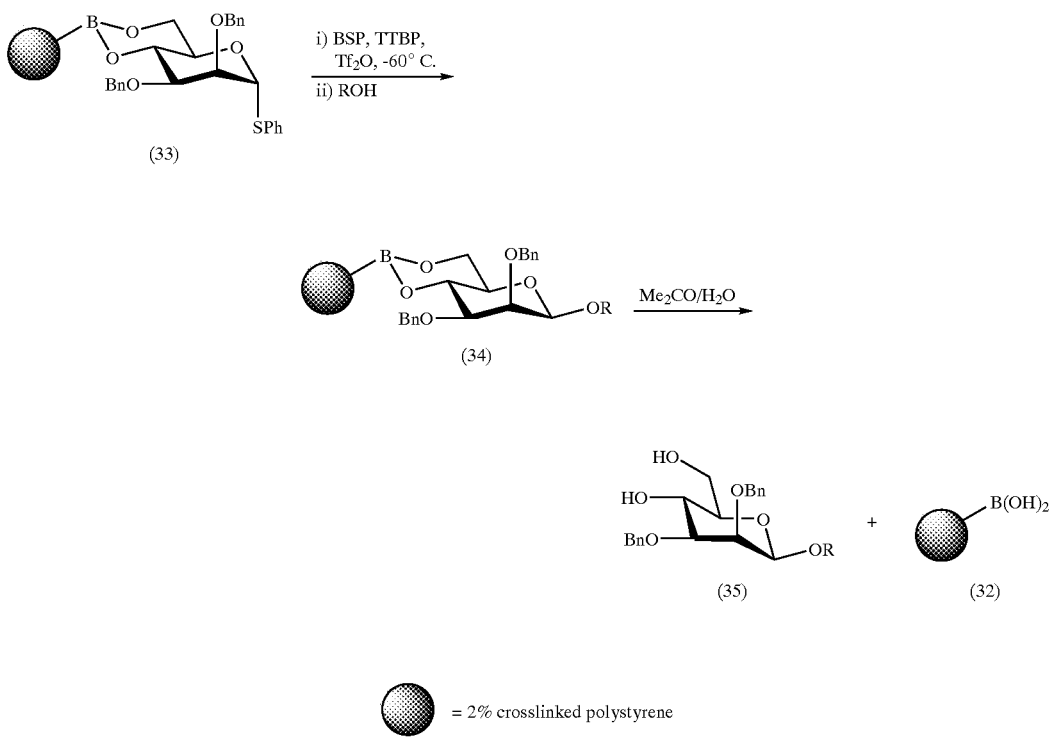

TABLE 3-continued
Polymer-supported Synthesis of β-Mannosides with Polystyrylboronate 10[a]
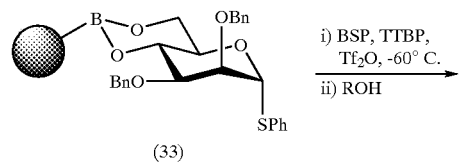
(33)
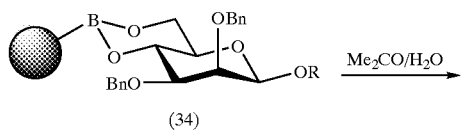
(34)
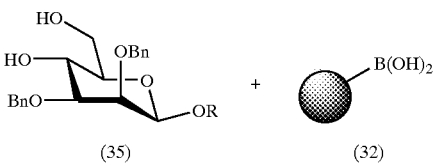
(35)    (32)
 = 2% crosslinked polystyrene
| Acceptor | Product[b] | Yield (%) | $^1J_{CH}$ (Hz) |
|---|---|---|---|
| 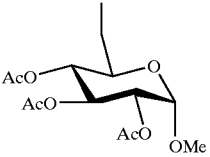 | 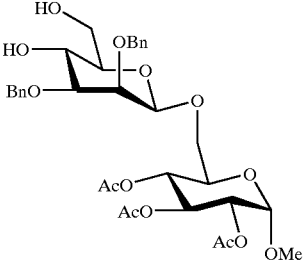<br>>9:1 | 73 | 155 |
| 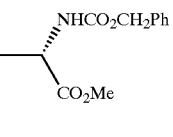 | 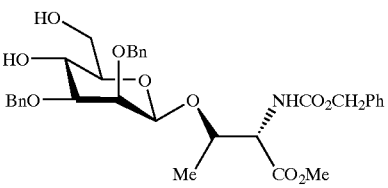<br>>9:1 | 79 | 154 |
| 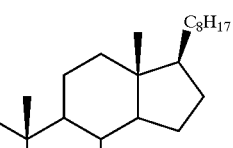 | 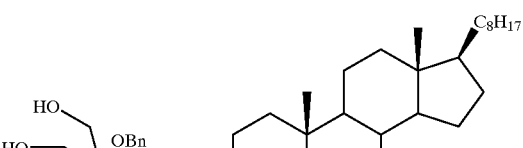<br>>9:1 | 78 | 154 |

TABLE 3-continued

Polymer-supported Synthesis of β-Mannosides with Polystyrylboronate 10[a]

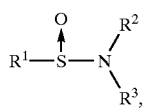

| Acceptor | Product[b] | Yield (%) | $^1J_{CH}$ (Hz) |
|---|---|---|---|
|  |  | 84 | 157 |
|  | >9:1 |  |  |

[a]All reactions were performed in $CH_2Cl_2$ at −60° C.;
[b]Anomeric ratios of >9:1 are conservative minima, in all such cases the minor isomer was not detected in the NMR spectra of the reaction mixtures.

In summary, the present invention is a powerful method for the polymer-supported synthesis of β-mannosides. The method utilizes BSP and $Tf_2O$ for the activaiton of thioglycosides. Very short activation times are required at a low temperature, and the isolated yields of β-mannosides from this polymer-supported protocol are directly comparable with those obtained using the analogous solution phase methodology. The method is both different and complimentary to that disclosed in Y Ito et al., *Angew, Chem. Int. Ed. Engl.* 33, 1765–1767 (1994) and M. Lergenmuller et al., *Eur. J. Org. Chem.*, 1367–1376 (1999). The present method differs fundamentally because cleavage from the resin is not an integral part of the coupling reaction, but rather the disaccharide is retained on the support The present method is complimentary to prior methods because, after cleavage, the method provides β-mannosides bearing free hydroxyl groups at the 4- and 6-positions, whereas the Ito et al. method provides the β-mannoside selectively deprotected at the 2-position.

Obviously, many modifications and variations of the invention as hereinbefore set forth can be made without departing from the spirit and scope thereof, and, therefore, only such limitations should be imposed as are indicated by the appended claims.

What is claimed is:

1. A method of forming a glycosidic bond comprising:
   (a) providing a thioglycoside having a thio moiety, SR, wherein R is aryl or alkyl;
   (b) activating the thioglycoside by treatment with
      (i) trifluoromethanesulfonic anhydride,
      (ii) a N,N-dialkylsulfinamide having a structure $$R^1-\overset{O}{\underset{\|}{S}}-N\overset{R^2}{\underset{R^3}{\diagup}},$$

wherein $R^1$ is selected from the group consisting of aryl, heteroaryl, and $C_{1-6}$alkyl; and $R^2$ and $R^3$, independently, are $C_{1-6}$alkyl, or $R^2$ and $R^3$ are taken together with the nitrogen atom to which they are attached to form a 4- to 8-membered aliphatic ring, optionally containing an additional nitrogen atom, an oxygen atom, or a sulfur atom;
and (iii) an optional sterically hindered base;
   (c) adding an alcohol or an amine to the activated thioglycoside to substitute an alcohol residue or an amine residue for the thio moiety of the thioglycoside by formation of the glycosidic bond.

2. The method of claim 1 wherein the mole ratio of thioglycoside:N,N-dialkylsulfinamide:trifluoromethanesulfuric acid is 1:1:1–1.2.

3. The method of claim 1 wherein the N,N-dialkylsulfinamide has a structure wherein $R^1$ is aryl, and $R^2$ and $R^3$, independently, are $C_{1-2}$alkyl or $R^2$ and $R^3$ are taken together with the nitrogen atom to which they are attached to form a 5- or 6-membered aliphatic ring.

4. The method of claim 1 wherein the N,N-dialkylsulfinamide has a structure in which $R^1$ is phenyl, and both $R^2$ and $R^3$ are methyl or ethyl, or $R^2$ and $R^3$ are taken together with the nitrogen, atom to which they are attached to form a piperidinyl moiety.

5. The method of claim 1 wherein the N,N-dialkylsulfinamide is

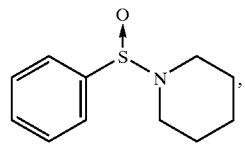

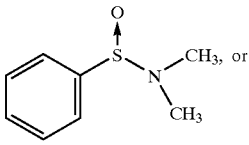

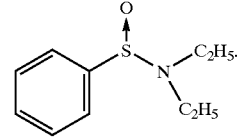

6. The method of claim 1 wherein the sterically hindered base comprises 2,6-di-t-butyl pyridine, 2,4,6-tri-t-butyl pyrimidine, or a mixture thereof.

7. The method of claim 1 wherein steps (b) and (c) are performed at −50° C. to −78° C.

8. The method of claim 1 wherein steps (b) and (c) are completed in about 2 to about 10 minutes.

9. The method of claim 1 wherein the alcohol is a primary, secondary, or tertiary alcohol having a structure R'''OH, and the alcohol residue has a structure —OR'''.

10. The method of claim 1 wherein the amine is a primary or secondary amine having a structure R'''NH$_2$ or (R''')$_2$NH, and the amine residue has a structure

or (R''')$_2$N—.

11. The method of claim 1 wherein the alcohol is selected from the group consisting of

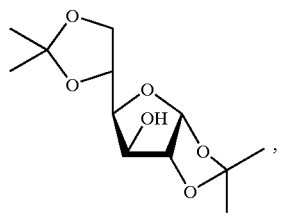 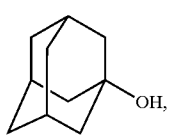

-continued

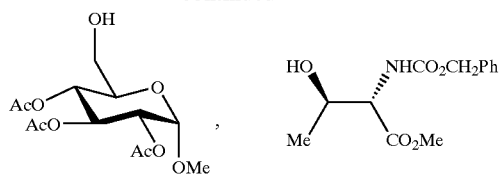

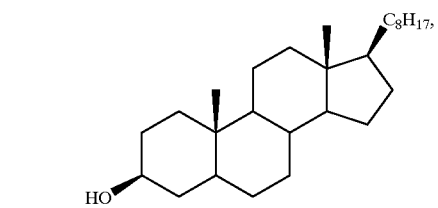

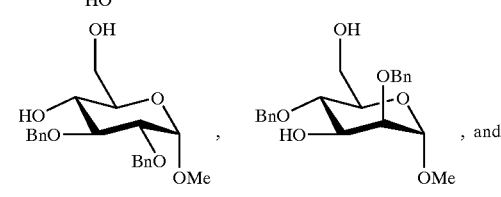

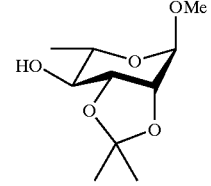

12. The method of claim 1 wherein the thioglycoside is selected from the group consisting of

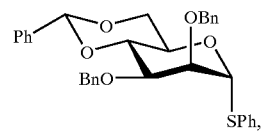 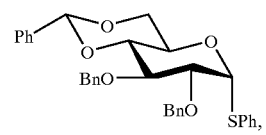

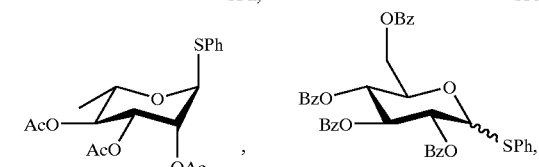

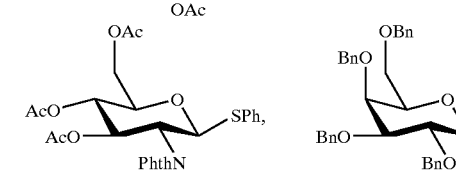

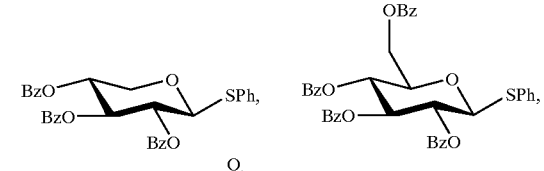

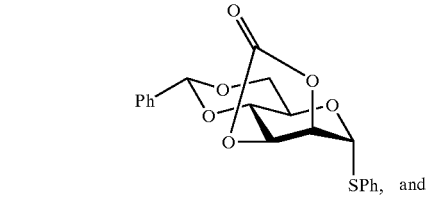

-continued

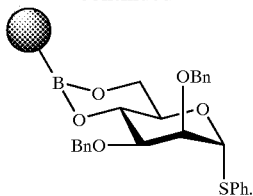

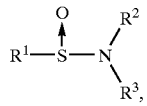 the symbol is a crosslinked polystyrene resin.

wherein the symbol ● is a cross-linked polystyrene resin.

13. The method of claim 1 performed in solution.

14. The method of claim 1 performed using a solid polymer support.

15. The method of claim 1 wherein the thioglycoside is protected with an ether group.

16. The method of claim 1 wherein the thioglycoside is protected with an ether group.

17. An activating system for a thioglycoside or a selenoglycoside comprising:
  (i) trifluoromethanesulfonic anhydride,
  (ii) a N,N-dialkylsulfinamide having a structure

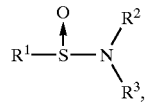

wherein R is selected from the group consisting of aryl, heteroaryl, and $C_{1-6}$alkyl; and $R^2$ and $R^3$, independently, are $C_{1-6}$alkyl, or $R^2$ and $R^3$ are taken together with the nitrogen atom to which they are attached to form a 4- to 8-membered aliphatic ring, optionally containing an additional nitrogen atom, an oxygen atom, or a sulfur atom;

and (iii) an optional sterically hindered base.

18. A method of synthesizing a β-mannoside in solid phase comprising the steps of:
  (a) reacting a thioglycoside having two hydroxy groups with a boronic acid functionalized polymer to form a bound thioglycoside donor;
  (b) activating the bound thioglycoside donor by a treatment with
    (i) trifluoromethanesulfonic anhydride,
    (ii) a N,N-dialkylsulfinamide having a structure

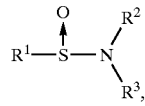

wherein R is selected from the group consisting of aryl, heteroaryl, and $C_{1-6}$alkyl; and $R^2$ and $R^3$, independently, are $C_{1-6}$alkyl, or $R^2$ and $R^3$ are taken together with the nitrogen atom to which they are attached to form a 4- to 8-membered aliphatic ring, optionally containing an additional nitrogen atom, an oxygen atom, or a sulfur atom;

and (iii) an optional sterically hindered base;

(c) adding an acceptor alcohol to the activated thioglycoside donor of step (b) to form a β-mannoside coupled to the boronic acid functionalized polymer; and (d) decoupling the β-mannoside from the boronic acid functionalized polymer.

19. A method of forming a glycosidic bond comprising:
  (a) providing a selenoglycoside having a seleno moiety, SeR, wherein R is aryl or alkyl;
  (b) activating the selenoglycoside by treatment with
    i) trifluoromethanesulfonic anhydride,
    (ii) a N,N-dialkylsulfinamide having a structure wherein $R^1$ is selected from the group consisting of aryl, heteroaryl, and $C_{1-6}$alkyl; and $R^2$ and $R^3$, independently, are $C_{1-6}$alkyl, or $R^2$ and $R^3$ are taken together with the nitrogen atom to which they are attached to form a 4- to 8-membered aliphatic ring, optionally containing an additional nitrogen atom, an oxygen atom, or a sulfur atom;

and (iii) an optional sterically hindered base;

(c) adding an alcohol or an amine to the activated selenoglycoside to substitute an alcohol residue or an amine residue for the seleno moiety of the selenoglycoside by formation of the glycosidic bond.

* * * * *

UNITED STATES PATENT AND TRADEMARK OFFICE
CERTIFICATE OF CORRECTION

PATENT NO. : 6,960,654 B2
APPLICATION NO. : 10/452734
DATED : November 1, 2005
INVENTOR(S) : David C. Crich It is certified that error appears in the above-identified patent and that said Letters Patent is hereby corrected as shown below:

Cover page, (57) Abstract, line 5, "oligosacchraides" should be -- oligosaccharides --

Column 39, line 13, "nitrogen, atom" should be -- nitrogen atom --

Column 41, line 20, "ether" should be -- ester --

Column 41, claim 17, line 33, "R" should be -- $R^1$ --

Column 42, claim 18, line 9, "R" should be -- $R^1$ --

Column 42, claim 19, line 26, "i)" should be -- (i) --

Signed and Sealed this

Twenty-first Day of November, 2006

JON W. DUDAS
*Director of the United States Patent and Trademark Office*